US00PP33363P2

(12) United States Plant Patent
Marczynski

(10) Patent No.: US PP33,363 P2
(45) Date of Patent: Aug. 17, 2021

(54) ***CLEMATIS* PLANT 'GOLDEN DREAM'**

(50) Latin Name: ***Clematis* hybrid**
Varietal Denomination: GOLDEN DREAM

(71) Applicant: Szczepan Marczynski, Pruszkow (PL)

(72) Inventor: Szczepan Marczynski, Pruszkow (PL)

( * ) Notice: Subject to any disclaimer, the term of this patent is extended or adjusted under 35 U.S.C. 154(b) by 0 days.

(21) Appl. No.: 17/079,721

(22) Filed: Oct. 26, 2020

(51) Int. Cl.
*A01H 6/72* (2018.01)
*A01H 5/02* (2018.01)

(52) U.S. Cl.
USPC ..... Plt./228

(58) Field of Classification Search
USPC ..... Plt./228
See application file for complete search history.

*Primary Examiner* — Annette H Para
(74) *Attorney, Agent, or Firm* — Cassandra Bright

(57) ABSTRACT

A new and distinct *Clematis* hybrid named 'GOLDEN DREAM' is disclosed, characterized by yellow flowers with a distinct maroon colored base. Plants begin flowering in Spring and rebloom throughout the Summer. Flowers are pendulous and have a light citrus scent. The new cultivar is a *Clematis* typically suited for ornamental container and landscape use.

2 Drawing Sheets

Figure 1:
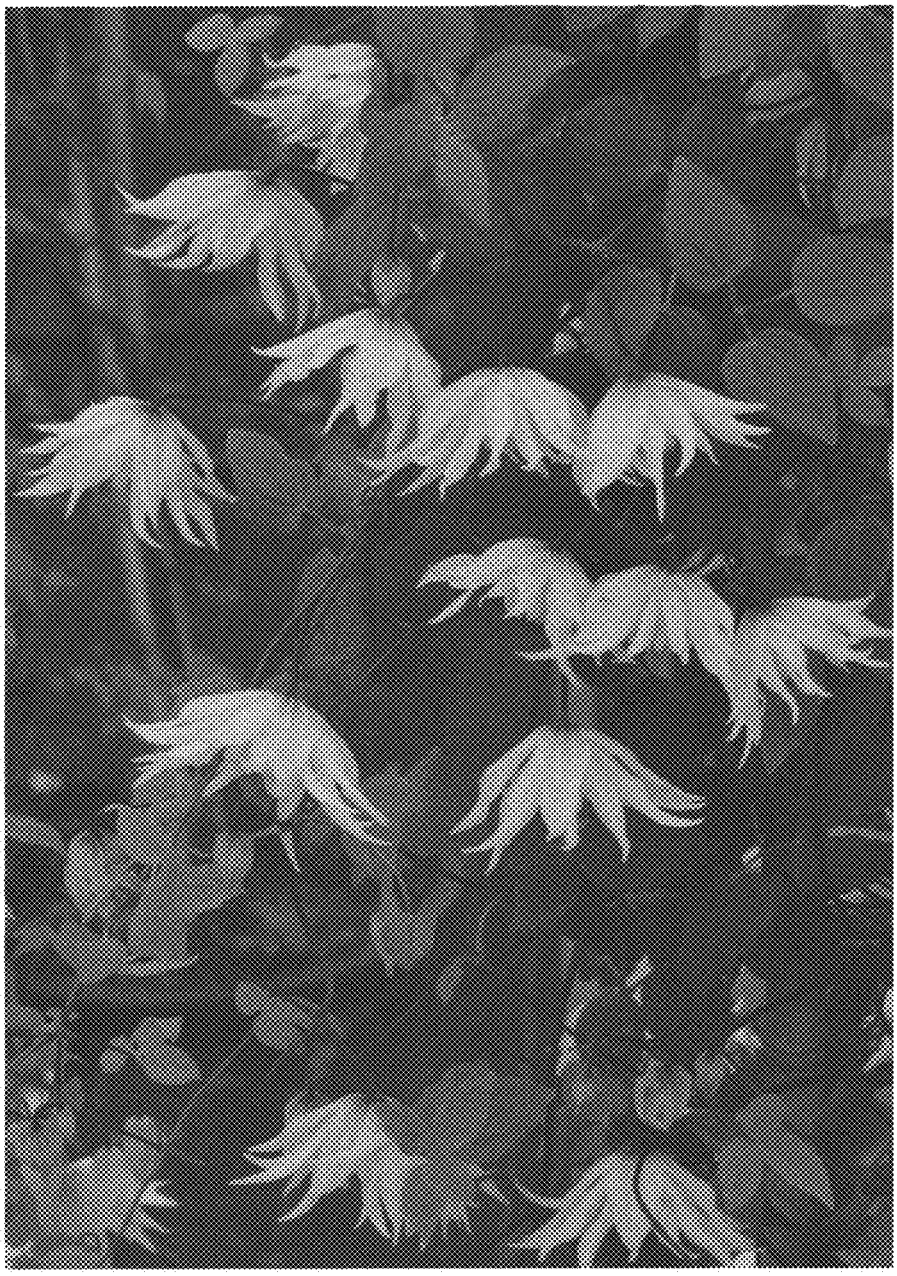

Latin name of the genus and species: *Clematis* hybrid.
Variety denomination: 'GOLDEN DREAM'.

BACKGROUND OF THE INVENTION

The new *Clematis* cultivar is a product of a planned breeding program conducted by the inventor, Szczepan Marczynski, in Pruszkow, Poland. The objective of the breeding program was to produce new compact *Clematis* varieties with novel or new colors. The cross resulting in this new variety was made during May of 2013.

The seed parent is the unpatented *Clematis* 'Lemon Bells'. The pollen parent is the unpatented *Clematis* 'Lemon Dream'. The new variety was identified as a potentially interesting selection in Spring of 2014 at a greenhouse in Pruszkow, Poland.

Asexual reproduction of the new cultivar 'GOLDEN DREAM' by softwood cuttings was first performed during June of 2015, at a greenhouse in Pruszkow, Poland. Subsequent propagation has shown that the unique features of this cultivar are stable and reproduced true to type in 4 successive generations.

SUMMARY OF THE INVENTION

The cultivar 'GOLDEN DREAM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GOLDEN DREAM.' These characteristics in combination distinguish 'GOLDEN DREAM' as a new and distinct *Clematis* cultivar:

1. Yellow flowers with a maroon base.
2. Flowering begins in Spring, reblooming occurs throughout the Summer.

3. Flowers have a light citrus scent.
4. Pendulous flowers.

PARENTAL COMPARISON

Plants of the new cultivar 'GOLDEN DREAM' are similar to plants of the seed parent in most horticultural characteristics however, plants of the new cultivar 'GOLDEN DREAM' differ in the following:

1. Flowers of the new variety are double and semi-double; flowers of the seed parent are single.
2. The new variety produces larger flowers, which have longer and wider petals than the seed parent.
3. Flowers of the new variety have a light citrus fragrance; flowers of the seed parent have no fragrance.

Plants of the new cultivar 'GOLDEN DREAM' are similar to plants of the pollen parent, in most horticultural characteristics, however, plants of the new cultivar 'GOLDEN DREAM' differ in the following;

1. Flowers of the new variety are double and semi-double; flowers of the pollen parent are entirely double.
2. Flowers of the new variety are smaller than flowers of the pollen parent.
3. Flowers of the new variety have a maroon base; flowers of the pollen parent are solid creamy yellow.
4. Petals of the new variety are not as undulating as petals of the pollen parent.

COMMERCIAL COMPARISON

Plants of the new cultivar 'GOLDEN DREAM' can be compared to the known commercial variety *Clematis* 'Zocoro', U.S. Plant Pat. No. 24,642. The *Clematis* varieties are similar in most horticultural characteristics, including their distinctive pendulous flowers, however, 'GOLDEN DREAM' differs from the comparator in the following:

1. Flowers of 'Golden Dream' are yellow and maroon; flowers of this comparator are pink.
2. Flowers of the new variety are completely pendulous, facing downward; flowers of 'Zocoro' face both outwards and downwards.

3. Petals of the new variety are wider than petals of this comparator.

BRIEF DESCRIPTION OF THE PHOTOGRAPHS

The accompanying photograph in FIG. 1 illustrates in full a typical plant of 'Golden Dream' in a three gallon pot, grown outdoors in Pruszkow, Poland. This plant is approximately 2 years old, grown outdoors.

Figure 2:
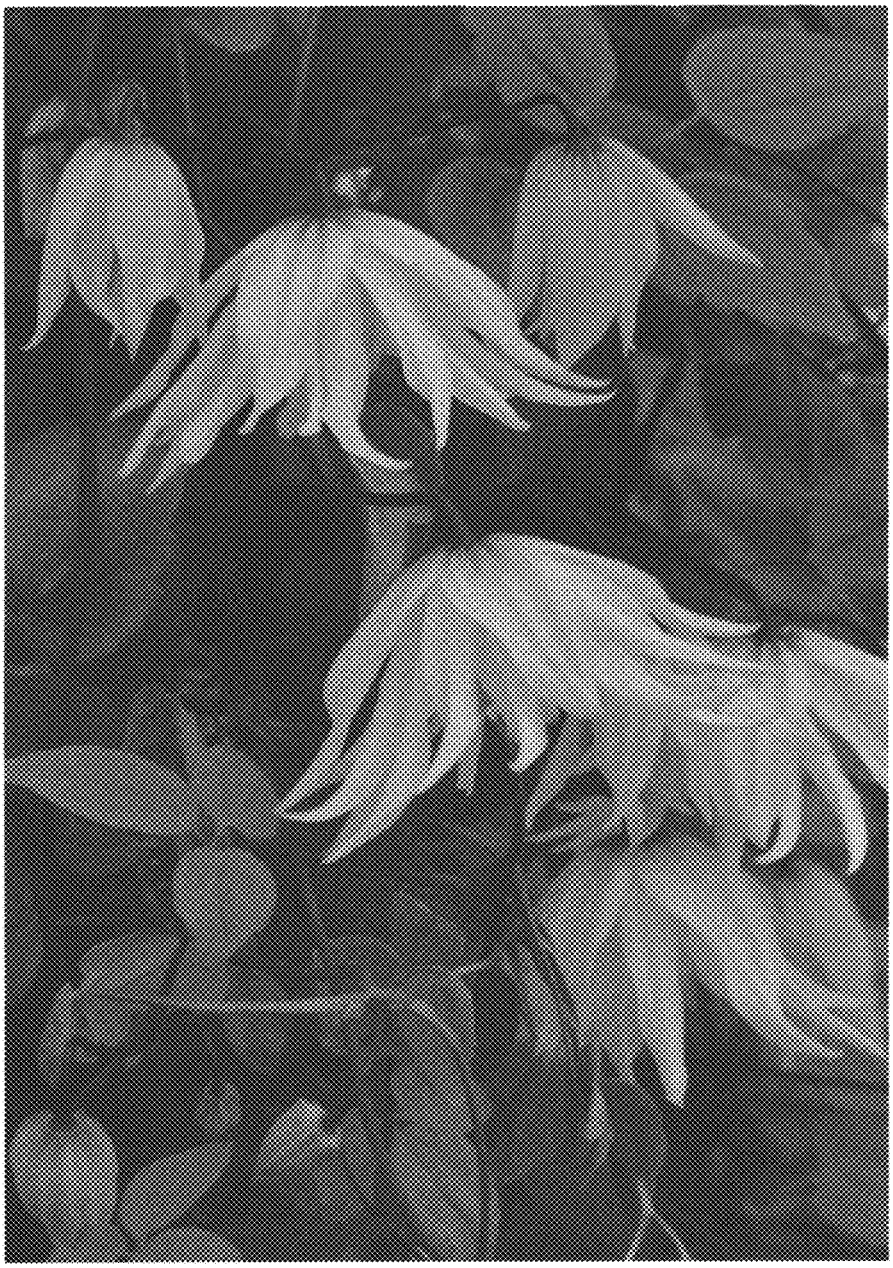

FIG. 2 illustrates a closer view of typical flowers and foliage of 'GOLDEN DREAM'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'GOLDEN DREAM' plants grown in a polyhouse in Grand Haven, Mich. The growing temperature ranged from approximately 5° C. to 10° C. at night to 18° C. to 27° C. during the day. No artificial light, photoperiodic treatments or chemical treatments were given to the plants. Measurements and numerical values represent averages of typical flowering types. Measurements were taken during June of 2020.

Botanical classification: *Clematis* hybrid 'GOLDEN DREAM'.

*Age of the plant described.*—Approximately 2 years old.

Propagation:

*Typical method.*—Stem cuttings.

*Time to initiate rooting.*—Approximately 30 days at about 20° C.

*Time to produce a rooted young plant.*—240 days at about 18-24° C.

*Root description.*—Free branching, dense, fine to medium, both fibrous and fleshy.

*Root color.*—White, not accurately measured with a color chart.

Plant:

*Growth habit.*—Perennial climbing vine.

*Height.*—Approximately 200 cm.

*Plant spread.*—Approximately 200 cm.

*Crop time to flower.*—1-2 years.

*Growth rate.*—150-200 cm per year.

*Quantity of lateral stems/branches.*—Average range, 5 to 6.

*Lateral stem/branch length.*—100 to 150 cm.

*Diameter of stems/branches.*—Approximately 4 mm.

*Stem color.*—Young: Near RHS Green 143C. Mature: Near RHS Greyed-Purple 187A.

*Lateral stem texture.*—Some pubescence.

*Internode length.*—Average 23 cm.

Foliage:

*Leaf.*—Arrangement and type: Opposite, ternate. Leaflets: Length: Average 6 cm. Width: Average 4 cm. Shape of blade: Ovate. Apex: Acute. Base: Truncate. Attachment: Stalked. Margin: Crenate. Texture of both surfaces: Glabrous, matte. Slight pubescence on underside midrib. Color: Young foliage upper side: Near RHS Green 143B. Young foliage under side: Near RHS Yellow-Green 147B. Mature foliage upper side: Near RHS Greyed-Green N189A. Mature foliage under side: Near RHS Green NN 137D. Venation: Type: Palmate. Venation color upper side: Near RHS Yellow-Green N144D. Venation color under side: Near RHS Green 143D.

*Petiole.*—Length: Average range 1-2 cm. Diameter: Approximately 1 to 2 mm. Texture: Slightly pubescent. Color: Upper: Near RHS Yellow-Green 144B mixed with Greyed-Purple N186C. Lower: Near RHS Yellow-Green 144C.

*Stipules/tendrils.*—Not observed.

Flower:

*Bloom period.*—

*Natural season.*—Beginning in Spring, reblooming throughout the Summer.

*Flower type.*—Double or semi-double.

*Flower aspect.*—Pendulous, downward facing.

*Flower longevity on plant.*—Approximately 10-14 days, after fully opened. Partly self-cleaning.

*Quantity of flowers per plant.*—About 12 to 40.

*Flower size.*—Diameter: Average 7.5 cm. Depth: Average 7.5 cm.

*Calyx shape.*—Campanulate.

*Bud.*—Shape: Narrow ovate. Length: Approximately 4 cm. Diameter: Approximately 2 cm. Color: Near RHS Yellow 4C, base Greyed-Purple 185C.

*Petal.*—Petal Shape: Narrow cordate. Number of Petals: 4 exterior; flat, 12 interior; flat or folded. Texture: Smooth, upper and lower surfaces. Petal appearance: Matte. Petal arrangement: Rotate, partly overlapping. Petal margin: Entire, undulate. Petal tip: Acute. Petal base: Truncate. Petal length: Average 4.5 cm. Petal width: Average 4 mm.

*Color: petals: when opening.*—Upper surface: Near RHS Yellow 4C. Base flushed Greyed-Purple 185C. Lower surface: Near RHS Yellow 4C. Fully opened: Upper surface: Near RHS Yellow 4C. Base flushed Greyed-Purple 185C. Lower surface: Near RHS Yellow 4C. Base flushed Greyed-Purple 185C.

*Petaloids.*—Arrangement: Clustered in center, curving inwards toward center. Shape: Strap-shaped. Number: About 35. Texture: Softly pubescent, upper and lower surfaces. Appearance: Matte. Margin: Entire. Apex: Acute. Base: Truncate. Length: Average 2 cm. width: Average 3 mm.

*Color: petaloids: when opening.*—Upper surface: Near RHS Yellow 4C. Slight basal coloration near Greyed-Purple 185C. Lower surface: Near RHS Yellow 4C. Slight basal coloration near Greyed-Purple 185C. Fully opened: Upper surface: Near RHS Yellow 4C. Slight basal coloration near Greyed-Purple 185C. Lower surface: Near RHS Yellow 4C. Slight basal coloration near Greyed-Purple 185C.

*Tepals.*—Shape: Elliptic. Number: 4. Texture: Smooth, upper and lower surfaces. Lower surface ridged. Appearance: Matte. Arrangement: Cruciform. Margin: Entire, slightly undulate. Apex: Acuminate. Base: Truncate. Length: Average 4.25 to 4.5 cm. Width: Average 1.25 cm.

*Color: tepals: when opening.*—Upper surface: Near RHS Yellow 4C. Base flushed Greyed-Purple 185A fading outward to 185C. Lower surface: Near RHS Yellow 4C. Base flushed Greyed-Purple 185A fading outward to 185C. Fully opened: Upper surface: Near RHS Yellow 4C. Lower surface: Near RHS Yellow 4C.

*Peduncle.*—Length: Average 2.5 cm. Diameter: Approximately 1.5 mm. Strength: Strong. Color: Near RHS Brown 200C.

*Fragrance.*—Light citrus fragrance.

Reproductive organs:

*Stamens.*—Number: Average 25 per flower. Anther length: Approximately 18 mm. Anther color: Near RHS Yellow-Green 145C. Anther shape: Elliptic. Filament length: Approximately 16 mm. Filament color: Near RHS Yellow-Green 145C. Pollen quantity: Moderate. Pollen color: Near RHS Yellow 4D.

*Pistil.*—Number: More than 100 clustered in center, somewhat fused, making it impossible to count. Length: Approximately 1.2 cm. Style length: Approximately 1 cm. Style color: Near RHS Yellow-green 150D. Stigma: Shape: Rounded. Color: Near RHS Yellow-Green 150D. Ovary color: Near RHS Yellow-Green 150D.

Other characteristics:

*Seeds.*—1 per flower Green 143B. Numerous achenes emerging out and arching down, colored Green 143D, 1.75 cm long, about 5 mm wide.

*Disease/pest resistance.*—Neither resistance nor susceptibility to normal diseases and pests of *Clematis* has been observed.

*Lowest tTemperature tolerant to.*—−32° C. to 36° C.

What is claimed is:

1. A new and distinct cultivar of *Clematis* hybrid plant named 'GOLDEN DREAM' as herein illustrated and described.

* * * * *